United States Patent
Urman et al.

(10) Patent No.: US 9,955,889 B2
(45) Date of Patent: May 1, 2018

(54) REGISTRATION MAPS USING INTRA-CARDIAC SIGNALS

(71) Applicant: BIOSENSE WEBSTER (ISRAEL) LTD., Yokneam (IL)

(72) Inventors: Roy Urman, Karkur (IL); Ronen Krupnik, Karmiel (IL); Liron Shmuel Mizrahi, Kiryat Bialik (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 720 days.

(21) Appl. No.: 14/531,112

(22) Filed: Nov. 3, 2014

(65) Prior Publication Data
US 2016/0120426 A1    May 5, 2016

(51) Int. Cl.
| | |
|---|---|
| A61B 5/044 | (2006.01) |
| A61B 5/06 | (2006.01) |
| A61B 5/04 | (2006.01) |
| A61B 5/042 | (2006.01) |
| A61B 5/00 | (2006.01) |
| A61B 5/0452 | (2006.01) |
| G06F 19/00 | (2018.01) |
| A61B 5/046 | (2006.01) |
| A61B 34/20 | (2016.01) |

(52) U.S. Cl.
CPC .......... *A61B 5/044* (2013.01); *A61B 5/04012* (2013.01); *A61B 5/0422* (2013.01); *A61B 5/0452* (2013.01); *A61B 5/066* (2013.01); *A61B 5/068* (2013.01); *A61B 5/7475* (2013.01); *A61B 5/7485* (2013.01); *G06F 19/3437* (2013.01); *A61B 5/046* (2013.01); *A61B 5/6852* (2013.01); *A61B 5/7264* (2013.01); *A61B 5/743* (2013.01); *A61B 2034/2051* (2016.02)

(58) Field of Classification Search
CPC ..... A61B 5/044; A61B 5/0452; A61B 5/7485; A61B 5/068; A61B 5/7475; A61B 5/0422; A61B 5/066; A61B 5/04012; A61B 5/7264; A61B 5/046; A61B 5/743; A61B 5/6852; A61B 34/10; G06F 19/3437
See application file for complete search history.

(56) References Cited

U.S. PATENT DOCUMENTS

| | | |
|---|---|---|
| 5,738,096 A | 4/1998 | Ben Haim Shlomo |
| 6,226,542 B1 | 5/2001 | Reisfeld |

(Continued)

FOREIGN PATENT DOCUMENTS

EP    1779787 A2    2/2007

OTHER PUBLICATIONS

U.S. Appl. No. 14/166,982, filed Jan. 29, 2014.
(Continued)

*Primary Examiner* — Peter Luong
(74) *Attorney, Agent, or Firm* — Louis J. Capezzuto

(57) ABSTRACT

Cardiac catheterization is facilitated by generating first and second electroanatomic maps of a heart of a subject and designating common spatial locations that correspond to first electrical events on the first electroanatomic map and second electrical events on the second electroanatomic map. The common spatial locations of the first electroanatomic map and the second electroanatomic map are aligned to establish an aligned map, and using the location data on the aligned map to guide a probe to a point of interest.

13 Claims, 4 Drawing Sheets

(56) References Cited

U.S. PATENT DOCUMENTS

| | | | |
|---|---|---|---|
| 6,301,496 B1 | 10/2001 | Reisfeld | |
| 6,814,733 B2 | 11/2004 | Schwartz Yitzhack | |
| 6,892,091 B1 | 5/2005 | Ben Haim Shlomo | |
| 6,997,924 B2 | 2/2006 | Schwartz | |
| 7,156,816 B2 | 1/2007 | Schwartz | |
| 7,517,318 B2 | 4/2009 | Altmann | |
| 7,536,218 B2 | 5/2009 | Govari | |
| 7,756,576 B2 | 7/2010 | Levin | |
| 8,320,711 B2 | 11/2012 | Altmann | |
| 2003/0023130 A1* | 1/2003 | Ciaccio | A61B 5/04011 600/12 |
| 2007/0049817 A1* | 3/2007 | Preiss | A61B 5/0422 600/407 |
| 2007/0055167 A1* | 3/2007 | Bullinga | A61B 5/04011 600/509 |
| 2008/0058657 A1 | 3/2008 | Schwartz | |
| 2009/0268955 A1 | 10/2009 | Koolwal et al. | |
| 2010/0016712 A1 | 1/2010 | Bartal et al. | |
| 2010/0317962 A1* | 12/2010 | Jenkins | A61B 34/20 600/411 |
| 2011/0160569 A1 | 6/2011 | Cohen et al. | |
| 2012/0035459 A1 | 2/2012 | Revishvili | |
| 2013/0066193 A1 | 3/2013 | Olson et al. | |
| 2014/0107512 A1 | 4/2014 | Greenspan | |
| 2014/0180062 A1* | 6/2014 | Amit | A61B 6/487 600/424 |
| 2014/0200467 A1 | 7/2014 | Strom et al. | |
| 2015/0173707 A1* | 6/2015 | Ohuchi | A61B 8/0883 345/424 |

OTHER PUBLICATIONS

U.S. Appl. No. 61/844,024, filed Jul. 9, 2013.
Wilson K. et al: "Mapping of Cardiac Electrophysiology Onto a Dynamic Patient-Specific Heart Model", IEEE Transactions on Medical Imaging, IEEE Service Center, Piscataway, NJ, US, vol. 28, No. 12 (Dec. 1, 2009) pp. 1870-1880, XP011281238, ISSN 0278-0062, DOI: 10.1109/TMI.2009.2021429.
EP Search Report EP 15 19 2627 dated Mar. 9, 2016.

* cited by examiner

REGISTRATION MAPS USING INTRA-CARDIAC SIGNALS

BACKGROUND OF THE INVENTION

Field of the Invention

This invention relates to medical imaging systems. More particularly, this invention relates to improvements in medical image analysis.

Description of the Related Art

Three-dimensional (3-D) images of internal organs are useful in many catheter-based diagnostic and therapeutic applications, and real-time imaging is widely used during surgical procedures. Ultrasound imaging is a relatively convenient mode of real-time imaging, though the resolution of real-time ultrasound images is generally not as good as the resolution obtained from other imaging modalities, such as computerized tomography (CT) and magnetic resonance imaging (MRI).

Methods for 3-D mapping of a heart using a position-sensing catheter are well known in the art. For example, U.S. Pat. No. 5,738,096 to Ben-Haim, whose disclosure is incorporated herein by reference, describes a position-sensing probe brought into contact with multiple points in the body to generate an anatomical map. Physiological properties, including electrical activity on the surface of the heart, may also be acquired by the catheter.

Commonly assigned U.S. Pat. No. 8,320,711 to Altmann et al., which is herein incorporated by reference, discloses creating an anatomical map by delineation of a 3-D image of the cavity based. The method involves automated segmentation of a 3-D image along a 3-D segmentation contour and enhancement of a 3-D map based on the segmentation contour.

A body-surface mapping technique for mapping the heart is disclosed in commonly assigned U.S. Patent Application Publication No. 2008/0058657 by Schwartz et al., which is herein incorporated by reference. A reliable endocardial map is obtained by constructing a matrix relationship between a small number of endocardial points and a large number of external receiving points using a multi-electrode chest panel. Inversion of the matrix yields information allowing the endocardial map to be constructed.

Another disclosure describing a body-surface method for mapping the heart is U.S. Patent Application Publication No. 2012/0035459 by Revishvili et al. On a set of surface electrocardiograms for each discrete moment of the cardiocycle, values of the heart electric field potential at points of ECG-recording are determined, and a value of the electric field potential at each point of the chest surface is calculated by interpolation. Based on data of any visualization methodology, boundaries of chest and lungs surfaces and of the heart epicardial surface are determined.

Registration of electroanatomical maps with anatomical landmarks produced by other modalities is known, for example, from U.S. Patent Application Publication No. 2007/0049817, and commonly assigned U.S. Pat. No. 7,517,318 to Altmann et al., which are herein incorporated by reference. The latter document discloses a technique of image registration comprising providing a pre-acquired image of the target and placing a catheter having a position sensor, an ultrasonic imaging sensor and an electrode, in the patient's body. Positional information of a portion of the catheter in the patient's body is determined using the position sensor and electrical activity data-points of a surface of the target are acquired using the electrode. An ultrasonic image of the target is obtained using the ultrasonic imaging sensor and positional information for the electrical activity data-points of the surface of the target is determined. An electrophysiological map of the target is generated based on the electrical activity data-points and the positional information for the electrical activity data-points. Positional information for any pixel of the ultrasonic image of the target is determined. The pre-acquired image and the electrophysiological map are registered with the ultrasonic image and the result displayed.

Using the methods disclosed in the above-noted U.S. Patent Application Publication No. 2007/0049817 and U.S. Pat. No. 7,517,318, features such as scar tissue in the heart, which typically exhibits lower voltage than healthy tissue in the electro-anatomical map, can be localized and accurately delineated on the three-dimensional image.

SUMMARY OF THE INVENTION

Registration of electroanatomical maps of the heart with anatomic landmarks may not always be optimum. According to disclosed embodiments of the invention, registration of images that specify locations commonly associated with electrical events observed using different techniques is performed. The electrical events on the images may be respectively identified by applying different algorithms or by acquisition using different systems. Location data from one map may be used in conjunction with the aligned location data of another map for example for catheter and device placement.

There is provided according to embodiments of the invention a method, which is carried out by generating a first electroanatomic map of a heart of a living subject, generating a second electroanatomic map of the heart, and designating common spatial locations that correspond to first electrical events on the first electroanatomic map and to second electrical events on the second electroanatomic map. The method is further carried out by aligning the common spatial locations of the first electroanatomic map and the second electroanatomic map to establish a set of aligned maps, and using the set of aligned maps to guide a probe to a point of interest.

A further aspect of the method includes displaying the set of aligned maps.

Yet another aspect of the method includes introducing a catheter into the heart to obtain electrical data for at least one of the first electroanatomic map and the second electroanatomic map.

Another aspect of the method includes analyzing the electrical data to determine local activation times at respective locations in the heart.

One aspect of the method includes analyzing the electrical data to determine dominant frequencies at respective locations in the heart.

One aspect of the method includes analyzing the electrical data to determine phase information at respective locations in the heart.

According to an additional aspect of the method, analyzing the electrical data includes converting or transforming a unit of measurement of the first electroanatomic map to be compliant with a unit of measurement of the second electroanatomic map.

According to still another aspect of the method, at least one of the first electroanatomic map and the second electroanatomic map is obtained by body surface mapping.

According to another aspect of the method, the first electroanatomic map is obtained by body surface mapping and the second electroanatomic map is obtained using an intracardiac mapping catheter.

According to yet another aspect of the method, the first electroanatomic map and the second electroanatomic map are obtained using an intracardiac mapping catheter.

There is further provided according to embodiments of the invention a data processing system including a processor, a visual display screen, and a memory accessible to the processor for storing programs and data objects therein. The programs include an electroanatomic map generator, an image registration program, an analysis program and a graphical user interface configured to present graphical information on the visual display screen. Execution of the programs causes the processor to perform the steps of: invoking the electroanatomic map generator to generate at least a first electroanatomic map of a heart of a living subject, generating a second electroanatomic map of the heart, invoking the analysis program to identify common spatial locations that correspond to first electrical events on the first electroanatomic map and second electrical events on the second electroanatomic map, and invoking the image registration program to align the common spatial locations of the first electroanatomic map and the second electroanatomic map to establish a third electroanatomic map.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

System Overview

Figure 1:
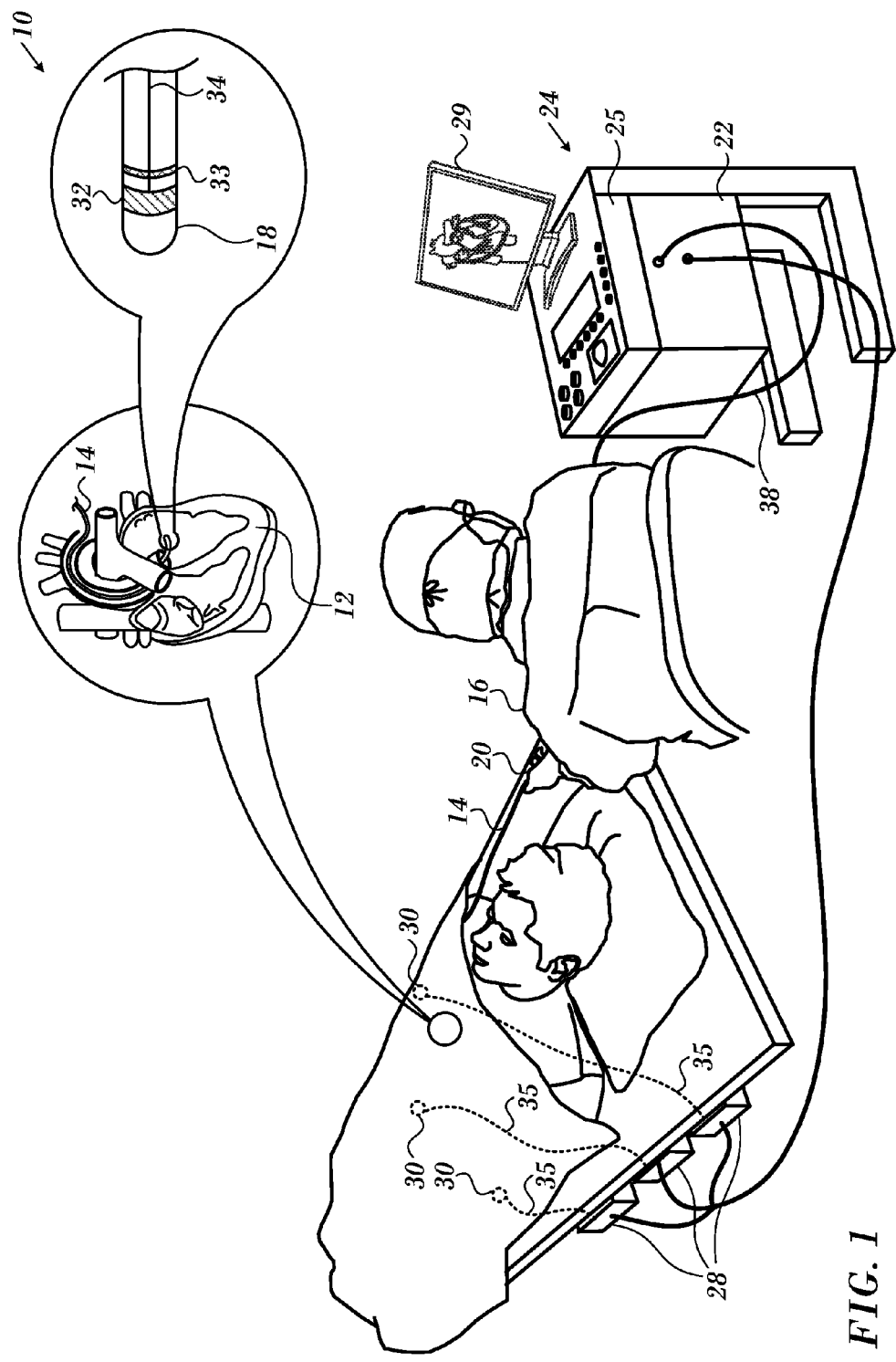
FIG. 1 is a pictorial illustration of a system for evaluating electrical activity in a heart of a living subject in accordance with an embodiment of the invention.

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, which is preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

In general, electroanatomic maps prepared using types of electrical signals or techniques are capable of identifying locations of anatomic landmarks, albeit by different expressions. For example particular landmarks may have identifying signatures on different functional maps, e.g., (1) known local activation times on a first map, measured for a reference point; and (2) characteristic electrogram morphology on a second map. The signatures may be patient-specific or general. The two maps can be placed in registration using the points identifying the electrical events. Many different electrical phenomena may identify points of interest on electroanatomic maps. Examples of such phenomena are include morphology of the first or second derivatives of unipolar electrograms, presence of multiple activation fronts, abnormal concentrations of activation vectors, and changes in the velocity vector or deviation of the vector from normal values. These phenomena may be mapped applying signal-processing and filtering techniques to electrical signals that are typically acquired by multi-electrode mapping catheters. Exemplary methods for such mappings are described in commonly assigned application Ser. No. 14/166,982 entitled Hybrid Bipolar/Unipolar Detection of Activation Wavefront, which is herein incorporated by reference.

In order to generate electroanatomic maps, the processor 22 typically comprises an electroanatomic map generator, an image registration program, an image or data analysis program and a graphical user interface configured to present graphical information on the monitor 29.

One map may be prepared from readings taken from unipolar intracardiac electrodes. Another map is typically, but not necessarily, prepared using a body surface technique, e.g., as described in the above-noted U.S. Patent Application Publication No. 2008/0058657. For example, one of the maps could be prepared using the ECVUE™ body-surface technique, available from CardioInsight Technologies, Inc., and another map prepared using the phase analysis method of the AMYCARD-01CTM™ diagnostic system, available from EP Solutions SA, Y-Parc Rue Galilée 7 Yverdon-les-Bains, Vaud 1400 Switzerland.

Many combinations of mapping techniques are possible, but in any case, common anatomic landmarks can be defined according to respective electrical events on the maps. The measurements in the maps should be compatible, which may require unit conversions or transformations to be performed so that the maps become interoperative.

Figure 2:
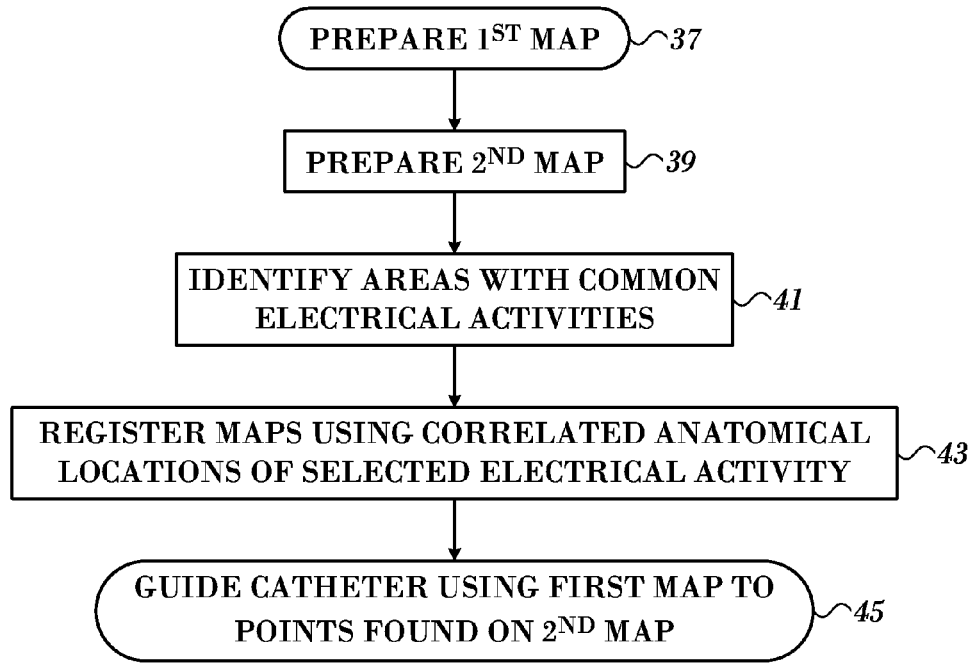
FIG. 2 is a flow-chart of a method for placing electroanatomic maps of the heart in registration to identify points of interest in accordance with an embodiment of the invention.

Reference is now made to FIG. 2, which is a flow-chart of a method for placing electroanatomic maps of the heart in registration to identify points of interest, in accordance with an embodiment of the invention. The process steps are shown in a particular linear sequence in FIG. 2 for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the process.

At initial step 37, a first electroanatomic map is prepared using a first method. Typically, this map is prepared by introducing a mapping catheter into the heart and taking multiple readings. The map may show, for example, wavefront propagation and local activation times at various points.

Next, at step 39, a second electroanatomic map is prepared. The second map includes the same areas of the heart as the map produced in initial step 37. The second map may be prepared, for example, by one of the body surface-mapping techniques described above, or may be a map acquired using a mapping catheter. Points of interest can be identified on the second electroanatomic map.

The first and second maps may be 2-dimensional or 3-dimensional. Indeed, when one or both of the maps are based on reconstruction of the heart from point clouds, the maps may involve a much larger number of dimensions. One method of cardiac reconstruction from a sparse point cloud is taught in commonly assigned Provisional Application No. 61/844,024 to Bar Tal et al., which is herein incorporated by reference.

Next, at step 41 areas having common electrical activities are identified on the first and second maps.

Next, at step 43 images of the first map and the second map are placed in registration. A minimum of three points on each of the maps should be used for the registration. A larger number of points tends to increase accuracy. The points used may include the points that were identified in step 41. Step 43 may be performed using the above-mentioned registration methods, including known point set registration techniques. Alternatively, the CARTOMERGE™ Image Integration Module, available from Biosense Webster, can be modified by those skilled in the art in order to perform step 41. In some embodiments, the registration may be based by identification of anatomic features that correlate with the electrical events. Additionally or alternatively the registration may be based on similarity of signal morphology, e.g., based on wavefront propagation, phase analysis, or voltage analysis. As a result of step 43, common anatomic areas of the two maps are aligned.

Next, at final step 45, the catheter is navigated to a target guided by the first electroanatomic map, modified by the addition of points that are identified on the second electroanatomic map. Optionally, an overlay comprising a registered set of images may be generated and displayed as a byproduct of step 43. Points of interest commonly identified on the may be indicated after registration by suitable visual cues or icons.

Figure 3:
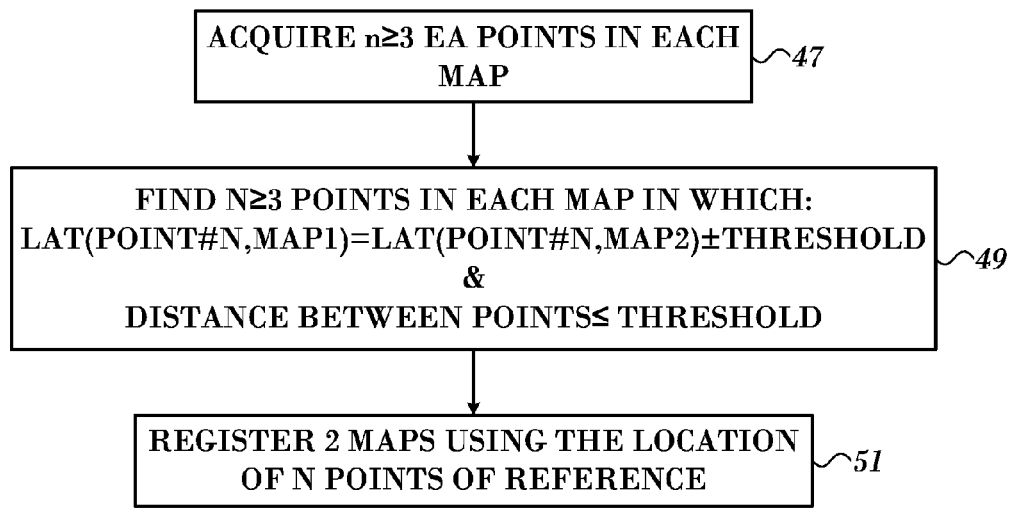
FIG. 3 is a detailed flow-chart describing a portion of the method shown in FIG. 2 in accordance with an embodiment of the invention.

Reference is now made to FIG. 3, which is a detailed flow-chart describing steps 41, 43 (FIG. 2), in accordance with an embodiment of the invention. In step 47, at least three corresponding electroanatomic points are identified in each of the two maps that were prepared in steps 39, 41 (FIG. 2).

Next, at step 49 at least three of the corresponding points obtained in step 47 are selected. The three points meet the following two criteria: (1) The local activation times (LAT) of the two points do not differ by more than a first threshold value; and (2) on each map the respective distances between the points do not exceed a second threshold value.

In step 51, the two maps are placed in registration using the location of the points of interest that were selected in step 49. Any suitable point set registration technique known in the art may be used.

Figure 4:
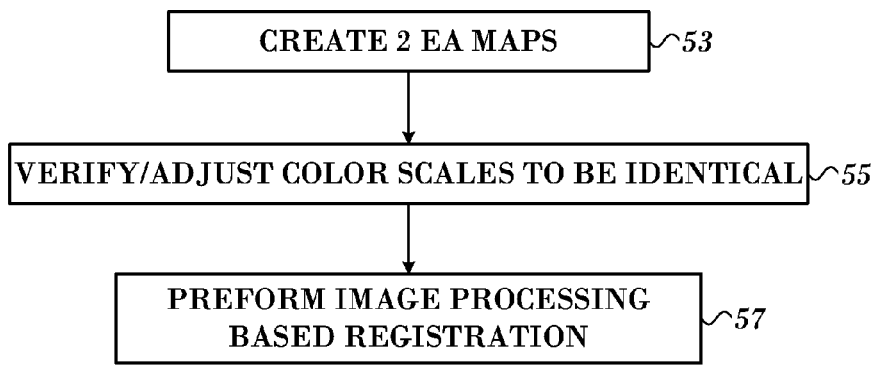
FIG. 4 is a detailed flow-chart describing a portion of the method shown in FIG. 2 in accordance with an alternate embodiment of the invention.

Reference is now made to FIG. 4, which is a detailed flow-chart describing steps 41, 43 (FIG. 2), in accordance with an alternate embodiment of the invention. The two electroanatomic maps are created in step 53. Such electroanatomic maps are typically displayed in pseudocolors that vary according to the electroanatomic function being displayed.

In step 55 the color scales of the maps prepared in step 53 are adjusted to conform to one another as closely as possible, taking into consideration interval changes that may have occurred in certain regions when the two maps were prepared at significantly different times. However, even then reference points typically remain unchanged and can be used as the basis of the adjustment.

In step 57, known image processing techniques are employed to register the two maps according to the color scales. Many such methods are known in the art based, e.g., on spatial or frequency intensity patterns, structural features, and various measures of similarity.

Figure 5:
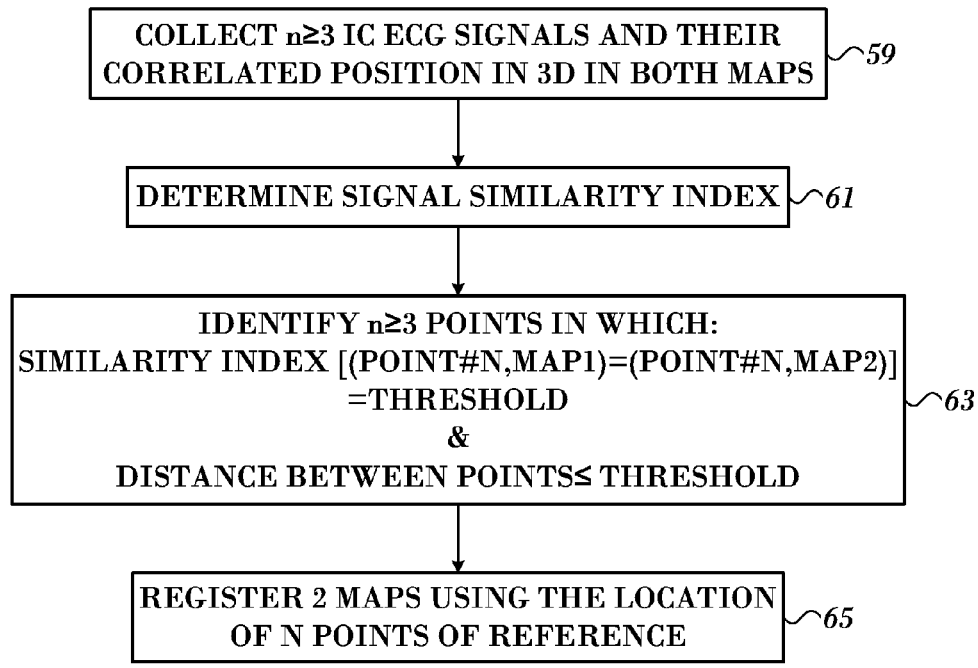
FIG. 5 is a detailed flow-chart describing a portion of the method shown in FIG. 2 in accordance with an alternate embodiment of the invention.

Reference is now made to FIG. 5, which is a detailed flow-chart describing steps 41, 43 (FIG. 2), in accordance with an alternate embodiment of the invention. At step 59 during preparation of the two maps, at least three intracardiac electrocardiogram (ECG) signals are obtained at corresponding locations.

Next, at step 61 a signal similarity index of corresponding ECG signals is determined. Such indices for determining signal similarity are known in the art.

Next, at least three of the corresponding points obtained in step 59 are selected. The three points meet the following two criteria: (1) the signal similarity index values of the two points equal or exceed a first threshold value; and (2) on each map the respective distances between the points do not exceed a second threshold value.

At step 65, the two maps are placed in registration using the location of the points of interest that were identified in step 59. Any suitable point set registration technique known in the art may be used.

Example 1

Figure 6:
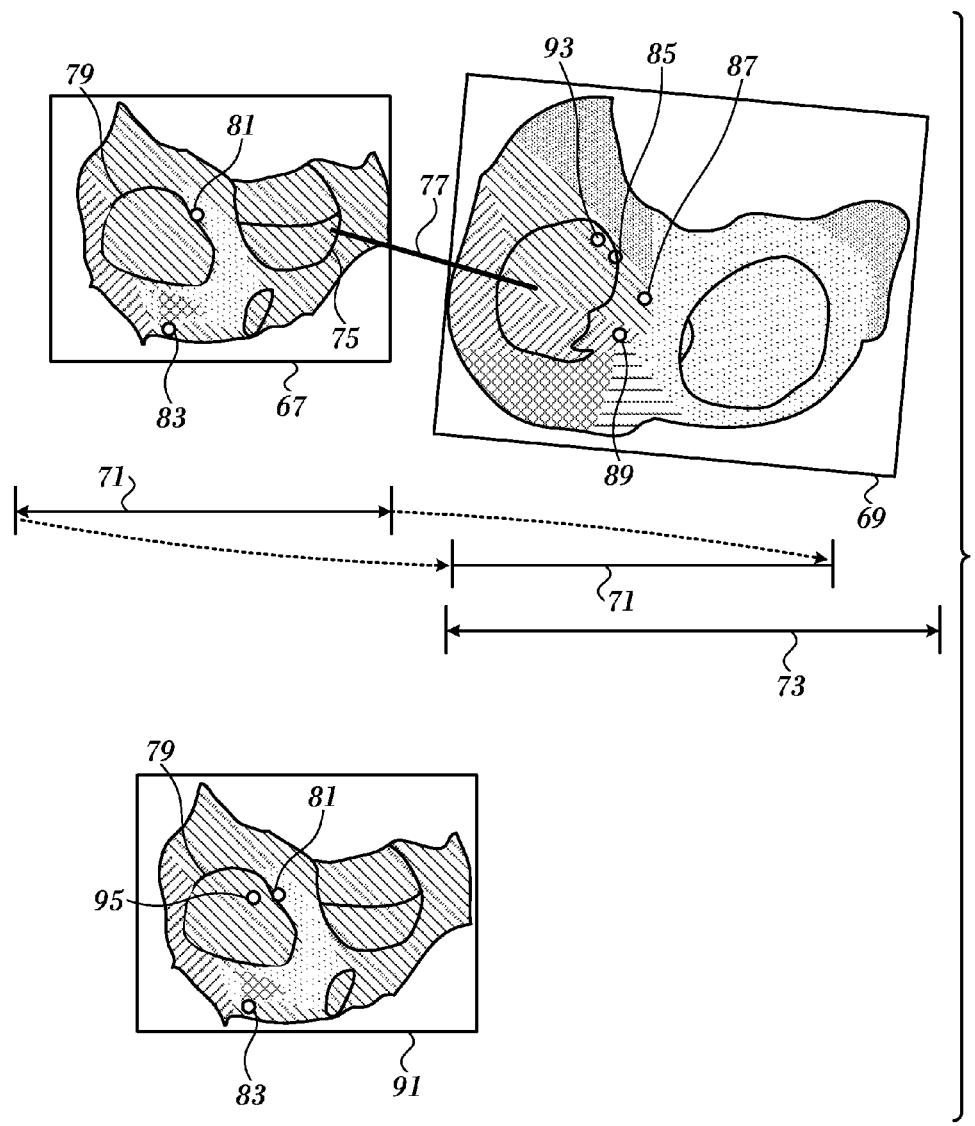
FIG. 6 shows electroanatomic maps of the heart, which are placed in registration, in accordance with an embodiment of the invention.

Reference is now made to FIG. 6, which shows two electroanatomic maps 67, 69 of the heart, which are to be placed in registration, in accordance with an embodiment of the invention. As the maps 67, 69 were prepared by different systems, their coordinate systems and scales are generally not identical. It will be noted by reference to the intervals 71, 73 that the scales of the maps 67, 69 differ. Moreover, the axes of rotation of the maps 67, 69 are not identical, as shown by intersecting lines 75, 77. Map 67 illustrates local activation times, and was prepared using a phase analysis mode of the above-noted CARTO system. Map 69 is an isochronous map that was prepared using a phase analysis mode of the AMYCARD-01C diagnostic system.

Points used to place the maps into registration can be appreciated on both maps 67, 69. For example, points 79, 81, 83 on map 67 and points 85, 87, 89 on map 69 all show corresponding electrical events that correspond anatomically to myocardium adjacent the annulus of the tricuspid valve and the apex of the right ventricle. These points can be used to register the maps 67, 69. At least three points should be used to register the maps. Accuracy increases when a larger number of points are employed.

Optionally, the maps 67, 69 can be overlaid to create a composite image (not shown). However, this is not essential, Instead, once the maps have been placed into registration, points of interest may be transformed from their coordinates on the map 69 to coordinates of the map 67. The modification of the map 67 in this manner is represented in FIG. 6 as a third map 91. The medical procedure may be carried out using the map 91, In this way it is possible to exploit the locations of the electrical events shown on the map 69 to navigate the catheter to a desired location using the techniques that produced the map 67, For example, coordinates of a location 93 (x, y) on the map 69 transform to coordinates (x', y') at location 95 on the map 91. The catheter can be guided to the location 95 using the map 91. The location 95 correctly identifies the location of the electrical event at location 93 on the map 69, It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:
1. A method, comprising of steps of:
using a first system to generate a first electroanatomic map of a heart of a living subject;
using a second system that is different to the first system to generate a second electroanatomic map of the heart;
identifying areas with common electrical events in the first and second electroanatomic maps and finding in those areas at least three points in each of the first and second electroanatomic maps where the local activation times of points in the first and second electroanatomic maps do not differ by more than a first threshold value and where the respective distances between the points on each electroanatomic map do not exceed a second threshold value;

using the at least three points to designate common spatial locations that correspond to first electrical events on the first electroanatomic map and second electrical events on the second electroanatomic map;

aligning the common spatial locations of the first electroanatomic map and the second electroanatomic map to establish a set of aligned maps; and using the set of aligned maps to guide a probe to a point of interest.

2. The method according to claim 1, further comprising the step of displaying the set of aligned maps.

3. The method according to claim 1, further comprising the step of: introducing a catheter into the heart to obtain electrical data for at least one of the first electroanatomic map and the second electroanatomic map.

4. The method according to claim 3, further comprising analyzing the electrical data to determine dominant frequencies at respective locations in the heart.

5. The method according to claim 3, further comprising analyzing the electrical data to determine phase information at respective locations in the heart.

6. The method according to claim 5, wherein analyzing the electrical data comprises converting or transforming a unit of measurement of the first electroanatomic map to be compliant with a unit of measurement of the second electroanatomic map.

7. The method according to claim 1, wherein at least one of the first electroanatomic map and the second electroanatomic map is obtained by body surface mapping.

8. The method according to claim 1, wherein the first electroanatomic map is obtained by body surface mapping and the second electroanatomic map is obtained using an intracardiac mapping catheter.

9. The method according to claim 1, wherein the first electroanatomic map and the second electroanatomic map are obtained using an intracardiac mapping catheter.

10. A data processing system comprising:
a processor;
a visual display screen; and
a memory accessible to the processor storing programs and data objects therein, the programs including an electroanatomic map generator, an image registration program, an analysis program and a graphical user interface configured to present graphical information on the visual display screen, wherein execution of the programs cause the processor to perform the steps of:

invoking the electroanatomic map generator to generate at least a first electroanatomic map of a heart of a living subject from a first system;

invoking the electroanatomic map generator to generate a second electroanatomic map of the heart from a second system different to the first system;

invoking the analysis program to analyze the first and second electroanatomic maps to identify areas with common electrical events in the first and second electroanatomic maps and finding at least three points in each of the first and second electroanatomic maps where the local activation times of points in the first and second electroanatomic maps do not differ by more than a first threshold value and where the respective distances between the points on each electroanatomic map do not exceed a second threshold value;

invoking the analysis program to identify common spatial locations that correspond to first electrical events on the first electroanatomic map and second electrical events on the second electroanatomic map; and invoking the image registration program to align the common spatial locations of the first electroanatomic map and the second electroanatomic map to establish a third electroanatomic map.

11. The system according to claim 10, wherein execution of the programs further cause the processor to invoke the graphical user interface to display the third electroanatomic map on the visual display screen.

12. The system according to claim 10, further comprising electrical circuitry adapted to receive signals, and the processor is operative to generate at least one of the first electroanatomic map and the second electroanatomic map from the signals.

13. The system according to claim 12, wherein the analysis program is operative for analyzing the signals to determine phase information at respective locations in the heart.

* * * * *